United States Patent
Melsheimer et al.

(10) Patent No.: US 8,475,403 B2
(45) Date of Patent: Jul. 2, 2013

(54) ASPIRATING AND INJECTING DEVICE WITH BIASED CLOSED DISTAL OPENING

(75) Inventors: Jeffry S. Melsheimer, Springville, IN (US); Christopher D. Bosel, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 189 days.

(21) Appl. No.: 12/849,432

(22) Filed: Aug. 3, 2010

(65) Prior Publication Data

US 2012/0035532 A1 Feb. 9, 2012

(51) Int. Cl.
*A61M 3/00* (2006.01)
(52) U.S. Cl.
USPC .......................................................... 604/43
(58) Field of Classification Search
USPC .................. 604/28, 43–45, 82–83, 164.01
See application file for complete search history.

(56) References Cited

U.S. PATENT DOCUMENTS

| | | |
|---|---|---|
| 2,564,977 A | 1/1949 | Hu |
| 3,757,771 A | 9/1973 | Ruegg et al. |
| 4,014,333 A * | 3/1977 | McIntyre .................... 604/43 |
| 4,099,528 A | 7/1978 | Sorenson et al. |
| 4,447,235 A | 5/1984 | Clarke |
| 4,874,368 A | 10/1989 | Miller et al. |
| 4,891,044 A | 1/1990 | Mitchell |
| 4,979,942 A | 12/1990 | Wolf et al. |
| 5,935,437 A | 8/1999 | Whitmore |
| 6,113,571 A | 9/2000 | Zinger et al. |
| 7,699,803 B2 * | 4/2010 | Nayak et al. .................... 604/72 |
| 2006/0264899 A1 | 11/2006 | Paul et al. |

OTHER PUBLICATIONS

Shiels, II, William E., "*Percutaneous treatment of lymphatic malformations*", Otolaryngology—Head and Neck Surgery, Aug. 2009, p. 219-224, vol. 141, No. 2.

* cited by examiner

*Primary Examiner* — Kevin C Sirmons
*Assistant Examiner* — Bradley Osinski
(74) *Attorney, Agent, or Firm* — Brinks Hofer Gilson & Lione

(57) ABSTRACT

A medical device for aspirating and injecting fluid into a body cavity for use with first and second syringes is provided. The medical device includes an outer needle having an outer lumen formed therethrough. A distal end of the outer needle is configured to puncture tissue for insertion of the needle into the body cavity. An inner cannula is disposed within the outer lumen and has an inner lumen formed therethrough. A distal end of the inner cannula is disposed within the outer lumen. A hub has a first hub opening for fluidly connecting the first syringe to the outer lumen and a second hub opening for fluidly connecting the second syringe to the inner lumen. The inner cannula extends from at least one of the first and second hub openings to the distal end of the inner cannula. A method for treating a cyst is also provided.

21 Claims, 4 Drawing Sheets

ASPIRATING AND INJECTING DEVICE WITH BIASED CLOSED DISTAL OPENING

BACKGROUND OF THE INVENTION

1. Field of the Invention

The present invention relates generally to medical devices and methods for aspiration, ablation, and/or injection in a bodily tissue or cavity, and more specifically to a medical device that uses a needle for aspiration, ablation, and/or injection.

2. Background

A lymphatic cyst, such as a macrocystic or microcystic lymphatic malformation, is one or more body cavities or sacs surrounded by a membrane, that may contain fluid, semi-fluid, air, or other material. A cyst typically has a distinct, relatively tough or thick membrane, which may consist of a layer of endothelium and connective tissue stroma. When it desirable to remove them, cysts are typically removed by open surgery.

Lymphatic cysts are often located and sized such that they adversely affect aesthetics, and open surgery to remove them could cause other adverse aesthetic affects, for example, scarring. Lymphatic cysts may also be too hazardous to remove by open surgery. For example, open surgery may result in significant complications, including nerve paralysis. Furthermore, reoccurrences are common, which may require additional surgery and associated risks. Therefore, it may be desirable to percutaneously treat such lymphatic cysts. However, percutaneous treatment of cysts typically involves multiple steps, devices, and medical personal.

Accordingly, further improvements and enhancements are needed for devices and methods of treatment of lymphatic cysts.

BRIEF SUMMARY OF THE INVENTION

In satisfying the above need and overcoming the above and other drawbacks and limitations of the known technology, the present invention provides a medical device and method for the percutaneous aspiration and ablation of cysts. A dual-lumen needle is inserted into a cyst percutaneously, such that one lumen of the needle is configured to aspirate fluid from the cyst, and another lumen of the needle is configured to inject fluid into the cyst.

One embodiment provides a medical device for aspirating and injecting fluid into a body cavity, such as a cyst, for use with first and second syringes, including an outer needle and an inner cannula. The outer needle has an outer lumen formed through the outer needle and a first opening at a distal end. The first opening is in fluid communication with the outer lumen. The distal end of the outer needle is configured to puncture tissue for insertion of the outer needle into the body cavity. The inner cannula is disposed within the outer lumen. The inner cannula has an inner lumen formed through the inner cannula and a second opening at a distal end of the inner cannula. The second opening is in fluid communication with the inner lumen. The distal end of the inner cannula is disposed within the outer lumen. The device further includes a hub having a first hub opening for fluidly connecting the first syringe to the outer lumen and a second hub opening for fluidly connecting the second syringe to the inner lumen. The inner cannula is disposed within the outer lumen from at least one of the first and second hub openings to the distal end of the inner cannula. At least one of the inner cannula and the outer needle is configured to aspirate fluid from the body cavity, and at least one of the inner cannula and the outer needle is configured to inject fluid into the body cavity.

Another embodiment provides a medical device for aspirating and injecting fluid into a body cavity, including an outer needle, an inner cannula, and first and second syringes. The outer needle has an outer lumen formed through the outer needle and a first opening at a distal end. The first opening is in fluid communication with the outer lumen. The distal end of the outer needle is configured to puncture tissue for insertion of the outer needle into the body cavity. The inner cannula is disposed within the outer lumen. The inner cannula has an inner lumen formed through the inner cannula and a second opening at a distal end of the inner cannula. The second opening is in fluid communication with the inner lumen. The distal end of the inner cannula is disposed within the outer lumen. A hub is attached to the outer needle and the inner cannula. The first syringe is fluidly connected to the outer lumen through a first hub opening, and the second syringe is fluidly connected to the inner lumen through a second hub opening. The inner cannula is coaxially disposed within the outer lumen from at least one of the first and second hub openings to the distal end of the inner cannula. At least one of the inner cannula and the outer needle is configured to aspirate fluid from the body cavity, and at least one of the inner cannula and the outer needle is configured to inject fluid into the body cavity.

In yet another embodiment, a method for the treatment of a cyst is provided. The method includes a step of inserting a dual-lumen needle device into a cyst. The dual-lumen needle device includes an outer needle having an outer lumen formed through the outer needle, and an inner cannula disposed within the outer lumen, wherein the inner cannula has an inner lumen formed through the inner cannula. The method also includes a step of aspirating fluid from the cyst through an aspiration lumen. The aspiration lumen is one of the outer lumen and the inner lumen. Further, the method includes a step of injecting an injection fluid into the cyst through an injection lumen. The injection lumen is the other of the outer lumen and the inner lumen that is not the aspiration lumen.

Further objects, features, and advantages of the invention will become apparent from consideration of the following description and the appended claims when taken in connection with the accompanying drawings.

DETAILED DESCRIPTION OF THE INVENTION

Figure 1:
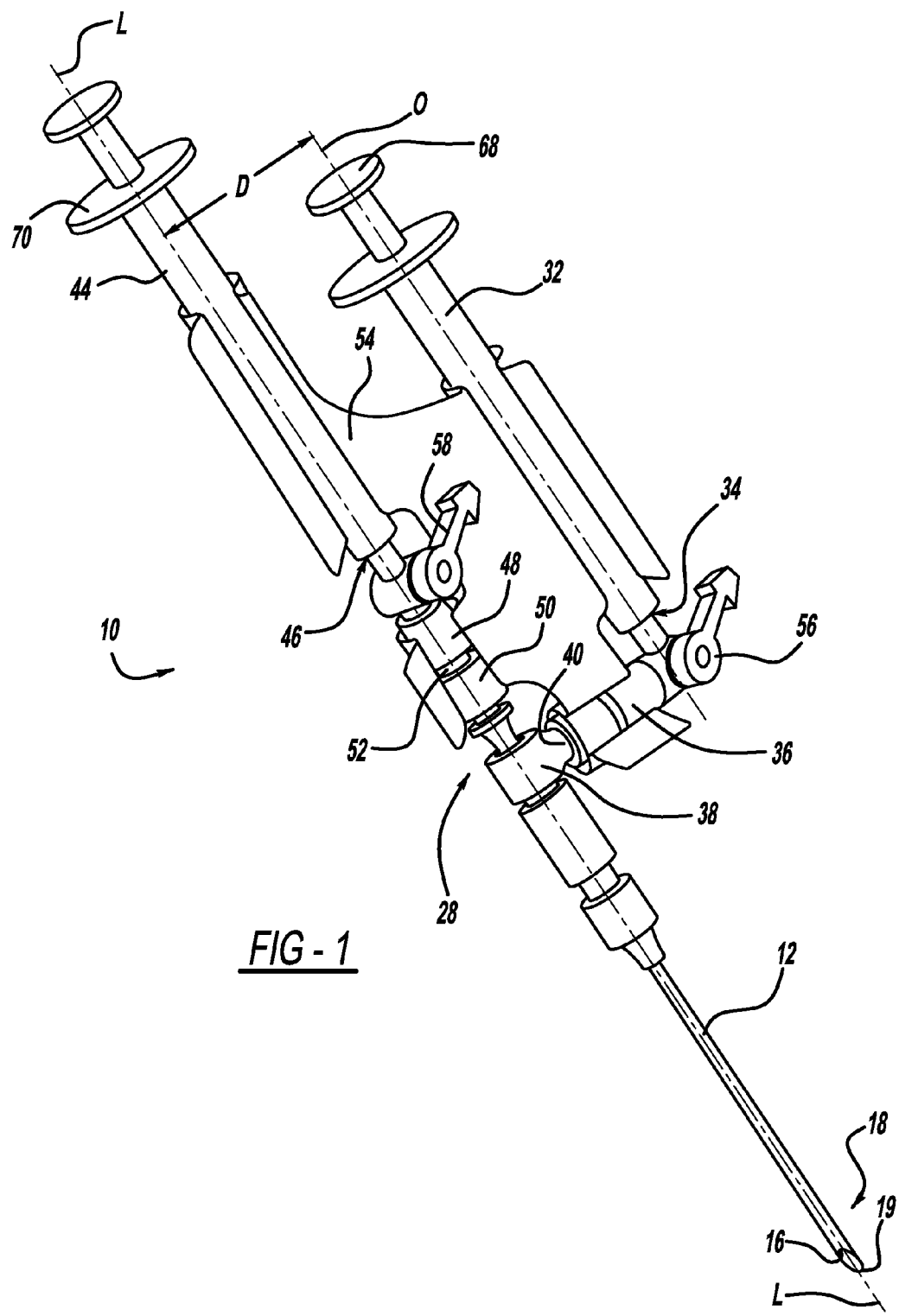
FIG. 1 is a perspective view of a medical device according to the principles of the present invention.

Detailed embodiments of the present invention are disclosed herein. It should be understood, however, that the disclosed embodiments are merely exemplary of the invention and may be embodied in various and alternative forms. The figures are not necessarily to scale; some figures may be configured to show the details of a particular component. Therefore, specific structural and functional details disclosed herein are not to be interpreted as limiting but merely as a representative basis for the claims and for teaching one skilled in the art to practice the present invention.

The present invention seeks to provide a dual-lumen needle/dual-syringe device that facilitates the ability to aspirate fluid from a cyst or other bodily cavity or sac and inject fluid into the cyst or other bodily cavity or sac from a single access point. The present invention provides a device and method for gaining access through the membrane of a cyst percutaneously, and the ability to aspirate, rinse, and remove fluid and particles from the cyst through the single access point, and to treat the cyst with a therapeutic treatment agent through the single access point, if desired.

Referring now to FIGS. 1-4, a medical device for aspirating and injecting fluid into a body cavity is generally indicated at numeral 10. The medical device 10 includes dual-lumen needle having a coaxial arrangement of a smaller diameter needle or cannula disposed within an overlying larger diameter needle or cannula. More specifically, the medical device 10 has an outer needle 12 having an outer lumen 14 formed through the center of the outer needle 12. In other words, the outer needle 12 is hollow. A first opening 16 is located at a distal end 18 of the outer needle 12. The first opening 16 is in fluid communication with the outer lumen 14.

The distal end 18 of the outer needle 12 comprises a tip 19 that is configured to puncture tissue for insertion of the outer needle 12 into the body cavity, such as a lymphatic microcyst or macrocyst. The tip 19, therefore, has an appropriate cutting feature for puncturing the membrane of a cyst, such as a trocar tip, bevel tip, or a Murphy's backside tip, by way of example. A variety of other grinds may also be used for the tip 19 of the distal end 18, without falling beyond the spirit and scope of the present invention.

Figure 2:
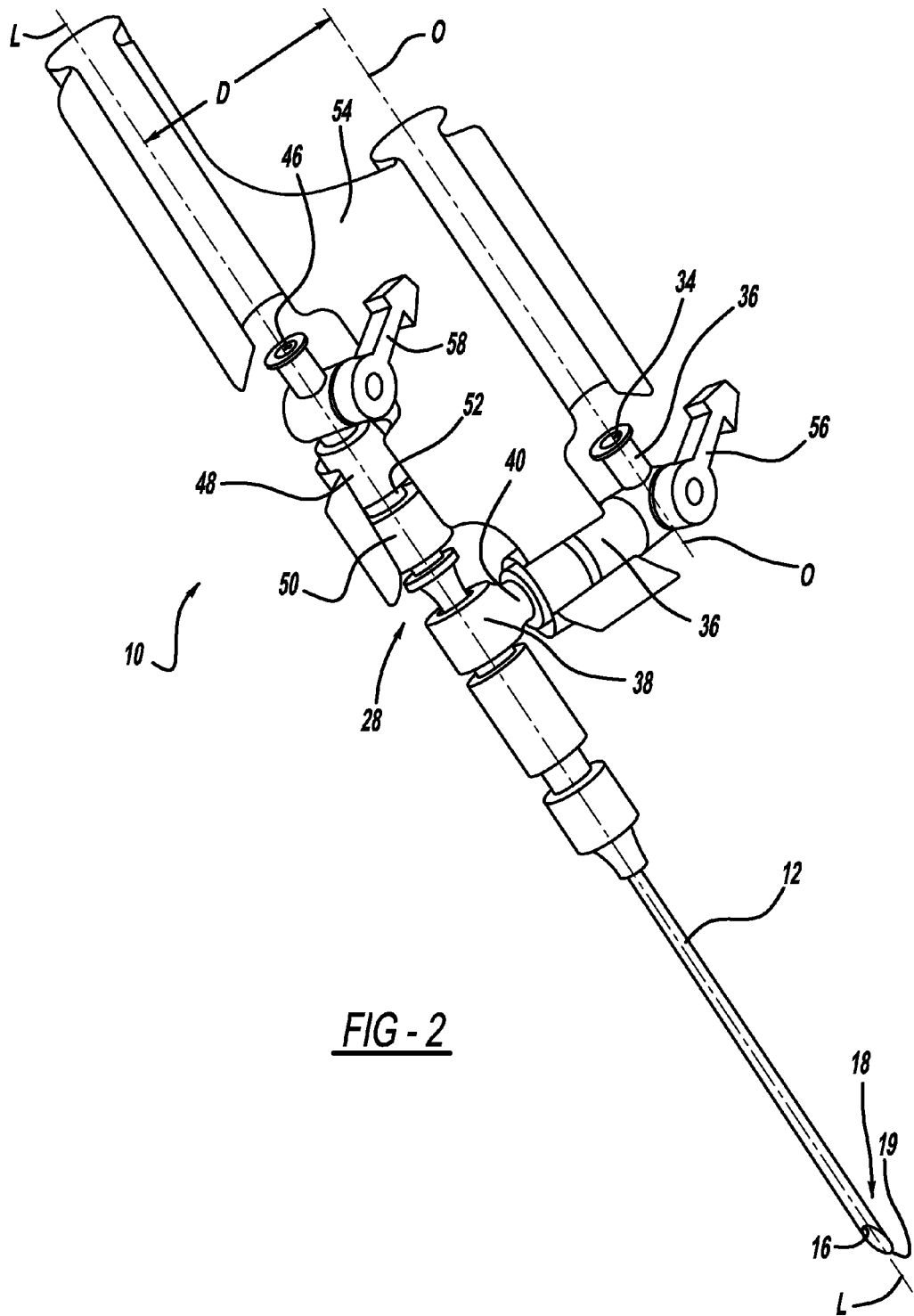
FIG. 2 is a perspective view of the medical device of FIG. 1, having the syringes removed, in accordance with the principles of the present invention.

Preferably, the tip 19 of the distal end 18 is very sharp such that it can puncture a tough membrane, such as that of a cyst. In some variations, the tip 19 of the distal end 18 is cut at an angle, as shown in FIGS. 1-2. The tip 19 could be cut at an angle having a range, for example, between 15° and 75° measured from the longitudinal axis L extending through the length of the needle 12. In some embodiments, the tip 19 could extend at an angle of about 45° from the longitudinal axis L extending through the length of the needle 12.

Figure 3:
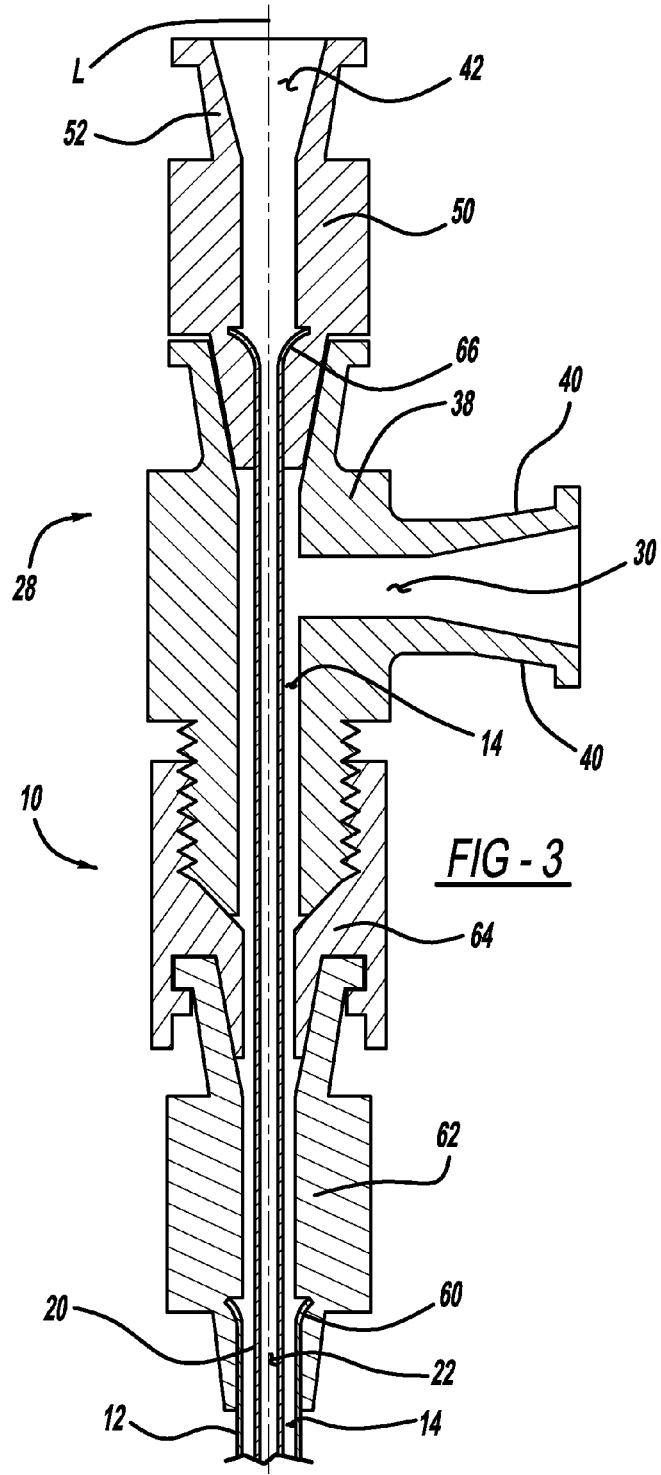
FIG. 3 is cross-sectional view of a portion of the medical device of FIGS. 1 and 2, in accordance with the principles of the present invention.
Figure 4:
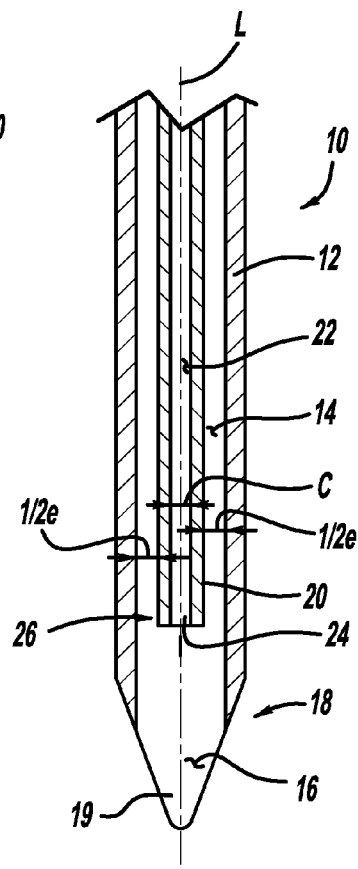
FIG. 4 is a cross-sectional view of another portion of the medical device of FIGS. 1-3, showing the distal ends of the outer needle and inner cannula, in accordance with the principles of the present invention.

Referring now to FIGS. 3-4, an inner needle or inner cannula 20 is disposed within the lumen 14 of the outer needle 12. The inner cannula 20 has an inner lumen 22 formed through the length of the inner cannula 20. The inner cannula 20 also has a second opening 24 at a distal end 26 of the inner cannula 20. The portions of the inner cannula 20 surrounding the second opening 24 may be flat, as shown in FIG. 4, or they may have any other suitable configuration, for example, the distal end 26 may be cut at an angle similar to the tip 19 of the distal end 18 of the outer needle 12.

The distal end 26 of the inner cannula 20 is disposed within the outer lumen 14. The distal end 18 of the outer needle 12 could be flush with the distal end 26 of the inner cannula 20; for example, both distal ends 18, 26 could extend to the same end point along the longitudinal axis L. In the alternative, the distal end 18 of the outer needle 12 could extend beyond the distal end 26 of the inner cannula 20 along the longitudinal axis L, as shown in FIG. 4.

The inner cannula 20 has a smaller outer diameter than the outer needle 12, such that the inner cannula 20 fits inside the outer lumen 14. The inner cannula 20 forms a lumen 22 extending therethrough having a lumenal diameter $c$; in other words, the inner diameter of the inner cannula 20 is defined as $c$. The outer lumen 14 has a diameter $o$; in other words, the inner diameter of the outer needle 12 is defined as $o$. However, the diameter of the clearance space of the outer lumen 14 (through which fluid may flow) is the outer lumen diameter $o$ minus the outer diameter of the inner cannula 20. The clearance space in the outer lumen 14 is located within the outer lumen 14 around the inner cannula 20. The diameter of the clearance space is defined as the effective outer lumen diameter $e$.

The effective outer lumen diameter $e$ (the outer lumen diameter $o$ minus the outer diameter of the inner cannula 20) may be about the same size as the inner lumen diameter $c$. Thus, an approximately equal cross-sectional area is provided for both the inner lumen 22 and the annular lumen (clearance space) formed by the outer lumen 14 and the inner cannula 20. In other words, the medical device 10 may be sized such that $e=c$ (effective outer lumen diameter $e$ equals inner lumen diameter $c$).

In other embodiments, the effective outer lumen diameter $e$ could be twice as large as the inner lumen diameter $c$, such that $e=2c$, or $c=\frac{1}{2}e$. In still other embodiments, the inner lumen diameter $c$ could be twice as large as the outer lumen effective diameter $e$, such that $c=2e$, or $\frac{1}{2}e=4c$. In the alternative, the inner lumen diameter $c$ and the outer lumen effective diameter $e$ could have any other suitable relationship, without falling beyond the spirit and scope of the present invention.

The outer needle 12 could have about a 17 gauge size (0.0575–0.0585 inch outer diameter), or in some instances, preferably a smaller diameter, for example, a 19 gauge size (0.0415–0.0425 inch outer diameter), by way of example. The size of the inner cannula 20 may be derived from the size of the outer needle 12, as described above.

The outer needle 12 and inner cannula 20 may be formed of any suitable material, such as biocompatible stainless steel (for example, stainless steel 304), Inconel, or Nitinol, by way of example. In the alternative, the inner cannula 20 could be formed of a polymer, such as polyethylene, polypropylene, PEEK, polycarbonate, polyamide, polyester, or any other plastic, by way of example. The outer needle 12 could also be made of a polymer, such as polyethylene, polypropylene, PEEK, polycarbonate, polyamide, polyester, or any other plastic, if desired.

The medical device 10 also includes a hub 28. The hub 28 has a first hub opening 30 that fluidly connects a first syringe 32 to the outer lumen 14. A first syringe canal 34 formed through one or more first syringe attachment pieces 36 fluidly connects the first hub opening 30 to the first syringe 32, in this embodiment. The first hub opening 30 is oriented perpendicular to the outer lumen 14 in this embodiment and is formed by a first hub piece 38 having a conical flange 40 extending therefrom to connect the first hub piece 38 to the first syringe attachment pieces 36.

The hub 28 further includes a second hub opening 42 that fluidly connects a second syringe 44 to the inner lumen 22. A second syringe canal 46 formed through one or more second syringe attachment pieces 48 fluidly connects the second hub opening 42 to the second syringe 44, in this embodiment. The second hub opening 42 is coaxially aligned with the inner lumen 22 and the outer lumen 14 along the longitudinal axis L. The second hub opening 42 may be formed by a second hub piece 50 having a conical flange 52 extending therefrom to connect the second hub piece 50 to the second syringe attachment piece(s) 48.

The inner cannula 20 is coaxially disposed within the outer lumen 14 along the longitudinal axis L from at least one of the first and second hub openings 30, 42 to the distal end 26 of the inner cannula 20. In this embodiment, the inner cannula 20 is coaxially disposed within the outer lumen 14 from the first hub opening 34 along the longitudinal axis L to the distal end 26 of the inner cannula 20. The longitudinal axis L extends centrally through the inner lumen 22 and the outer lumen 14. The second hub opening 42 is coaxially aligned with the outer lumen 14 and the inner lumen 22 along the longitudinal axis L to provide coaxial alignment between the inner and outer lumens 14, 22 and the second syringe 44. Therefore, the inner cannula 20 is concentrically located within the outer lumen 14 of the outer needle 12. In other embodiments, the inner cannula 20 may be disposed within the outer lumen 14 off-center from the longitudinal axis L, such that the inner cannula 20 is not coaxially, and not concentrically, disposed in the outer lumen 14. For example, the inner cannula 20 could be disposed in contact with a portion of the inner wall of the outer lumen 14, by way of example.

The first syringe 32 defines an offset axis O that extends centrally through the lumen of the first syringe 32. The first syringe 32 may be offset a distance D from the longitudinal axis L, or from the second syringe 44. For example, the offset axis O may be offset a distance D from the longitudinal axis L. The offset axis O may be generally parallel to the longitudinal axis L. Thus, the first and second syringes 32, 44 are arranged parallel to each other. In this embodiment, the distance D is large enough that the first and second syringes 32, 44 remain free from contact with each other when the medical device 10 is operated.

The hub 28 includes a hub body 54 that is connected to the syringes 32, 44 in this embodiment. The hub body 54 clamps onto each syringe 32, 44 and onto the first and second syringe attachment pieces 36, 48. In this embodiment, the hub body 54 also clamps around the second hub piece 50, but not around the first hub piece 38. The hub body 54 is configured to hold the various parts of the medical device 10 together, however, it should be understood that any other suitable means could be used, without falling beyond the spirit and scope of the present invention.

The medical device 10 may further include valves, such as stopcocks 56, 58 or one-way valves, such as check valves. The valves may be operable to restrict fluid from flowing through the first and second hub openings 30, 42. In this embodiment, the medical device 10 includes a first stopcock 56 fluidly connected to the first hub opening 30 and operable to restrict fluid from flowing through the first hub opening 30; and a second stopcock 58 fluidly connected to the second hub opening 42 and operable to restrict fluid from flowing through the second hub opening 42. In the alternative, the plungers of the syringes 32, 44 could be configured such that pressure holds the fluids therein and valves such as stopcocks 56, 58 are not needed. In another variation, a gun-type configuration may be used, including triggers to operate the syringes 32, 44 and/or the valves 56, 58.

The hub body 54 provides an assembly for the hub 28 and syringes 32, 44 that may allow for manipulation of the syringes 32, 44 with one hand, while allowing another hand to manipulate the stopcocks 56, 58 to distribute fluid to and from the syringes 32, 44. Preferably, the medical device 10 can accommodate a variety of syringes. For example, the syringes 32, 44 may be removable to use different injection fluids, by way of example. Further, the attachment pieces 36, 48 and hub body 54 that attach to the syringes 32, 44 may be configured to accommodate various sizes of syringes 32, 44.

The outer needle 12 has a proximal end 60, opposite its distal end 18, that may be fixedly attached to the hub 28, for example, by fitting the proximal end 60 to a first hub part 62 that is attached to a second hub part 64, which is attached to the first hub piece 38. Therefore, the outer needle 12 is fixedly attached to the hub 28. It should be understood that the first and second hub parts 62, 64 are optional; any number of hub parts 62, 64 or no hub parts 62, 64 at all may be used. For example, the proximal end 60 of the outer needle 12 may be fixedly attached directly to the first hub piece 38, or the hub 28 may be unitarily formed without distinct first and second hub pieces 38, 50, in which case, the outer needle 12 may be fixedly attached to the unitarily formed hub 28. In still other variations, the outer needle 12 may be unitarily formed with the hub 28, or the outer needle 12 may be moveable with respect to the hub 28 (i.e., not fixedly attached thereto). In some embodiments, one or more parts of the medical device 10 may be injection molded or ultrasonically injection molded, by way of example.

The inner cannula 20 has a proximal end 66, opposite its distal end 26, that may be fixedly attached to the hub 28, for example, by fitting the proximal end 66 to the second hub piece 50. Therefore, the inner cannula 20 is fixedly attached to the hub 28. However, like the proximal end of the outer needle 12, the proximal end 66 of the inner cannula 20 may be connected to the hub 28 in any number of ways; for example, it could be connected to the first hub piece 38 or another hub part (not shown). In the alternative, the proximal end 66 of the inner cannula 20 may be attached to a unitarily formed hub 28 (without distinct first and second hub pieces 38, 50), or the inner cannula 20 may be unitarily formed with the hub 28. In some variations, the inner cannula 20 may be moveable with respect to the hub 28 (i.e., not fixedly attached thereto).

The arrangement of fixedly attaching one or both of the inner cannula 20 and the outer needle 12 to the hub 28 may allow the outer lumen 14 and the inner lumen 22 to be fixed and sealed with respect to each other, such that fluid may not flow between the outer lumen 14 and the inner lumen 22 within the hub 28. In turn, the syringes 32, 44 may also be fixedly attached to the hub 28, so that the fluid within each syringe 32, 44 is not mixed with the fluid of the other syringe 32, 44 outside of the patient. In other words, the first syringe 32 is fluidly connected to the outer lumen 14 and is sealed from the inner lumen 22 and the second syringe 44. Likewise, the second syringe 44 is fluidly connected to the inner lumen 22 and is sealed from the outer lumen 14 and the first syringe 32.

In some embodiments, one or both of the syringes 32, 44 may be permanently fixed to the hub 28; or one or both of the syringes 32, 44 may be removably fixed to the hub 28. For example, if the outer needle 12 is to be used for aspiration, the first syringe 32, which is fluidly connected to the outer lumen 14, may be permanently fixed to the hub 28, while the second syringe 44 is removably fixed to the hub 28. As such, the second syringe 44 filled with a rinsing fluid may be attached and the fluid may injected, and then another second syringe 44 filled with another fluid, such as another rinsing fluid or a treatment agent, may be attached to the hub 28 and the fluid may be injected through the inner cannula 20 into the body cavity.

The first hub opening 30 may be longitudinally displaced along the longitudinal axis L from the second hub opening 42. Accordingly, the first and second syringes 32, 44 may be longitudinally displaced from each other along the longitudinal axis L. Therefore, the handle 68 of the pump of the first syringe 32 is longitudinal displaced from the handle 70 of the pump of the second syringe 44. The handles 68, 70 and the hands operating them are thus provided with more clearance space than would be provided if the syringe handles 68, 70 were located at the same point longitudinally, as measured along the longitudinal axis L.

At least one of the inner cannula 20 and the outer needle 12 is configured to aspirate fluid from a body cavity, and at least one of the inner cannula 20 and the outer needle 12 is configured to inject fluid into the body cavity. For example, the outer needle 12 may be configured to aspirate fluid from a body cavity, while the inner cannula 20 may be configured to inject fluid into a body cavity. In some embodiments, one or both of the inner cannula 20 and the outer needle 12 may be configured to perform both aspiration and injection.

To make the medical device 10, the hub 28, including its various hub parts 62, 64 and hub pieces 38, 50 may be fabricated to fit the outer needle 12 and the inner cannula 20. The outer needle 12 may be ground with a very sharp bevel to provide a sharp tip 19 for penetrating a tough cystic membrane. The inner cannula 20 may be deburred and trimmed to length to fit within the outer lumen 14. The inner cannula may be affixed to the hub 28, and the outer needle 12 may be checked for desired length before being affixed to the hub 28. Attachment pieces 36, 48 and stopcocks 56, 58 may be fitted to the hub 28. The hub body 54 may be clamped to the hub 28 and/or one or more of the attachment pieces 36, 48 or other parts of the medical device 10 if desired.

Figure 5:
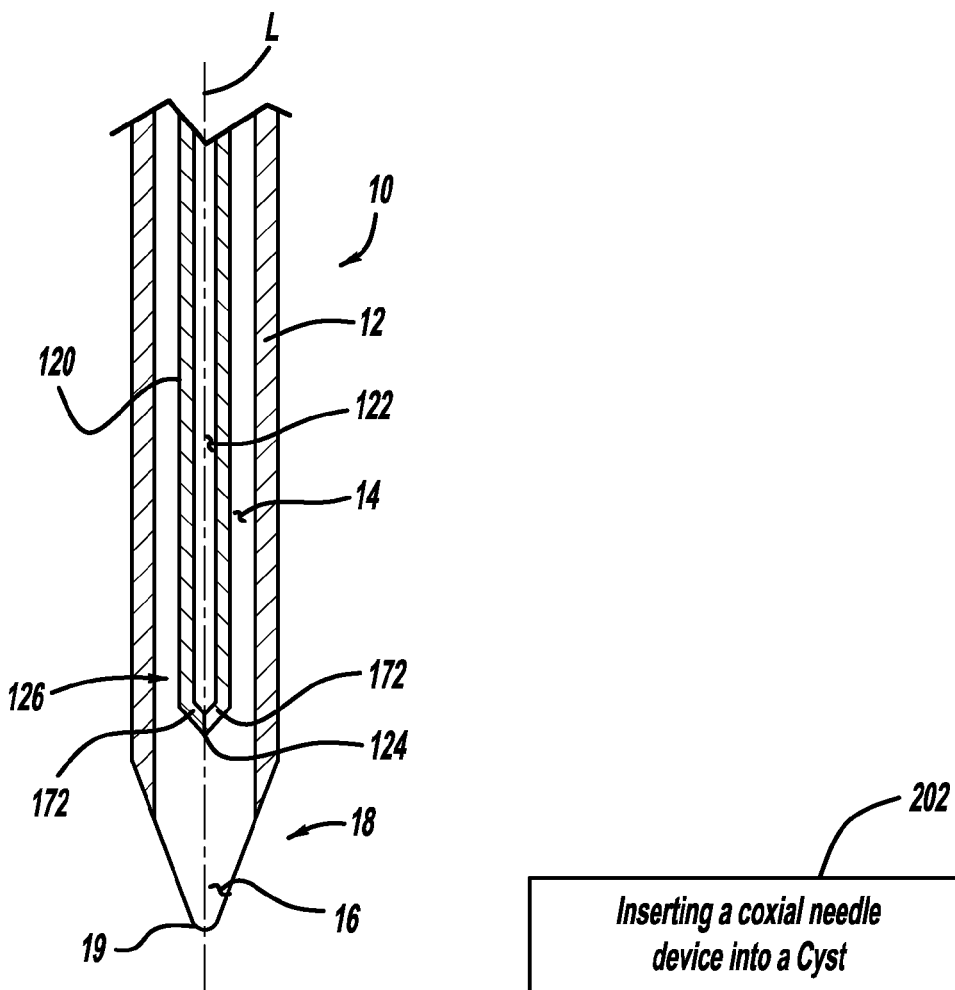
FIG. 5 is cross-sectional view of another embodiment of the distal ends of the outer needle and an inner cannula of the medical device of FIGS. 1-3, according to the principles of the present invention.

Referring now to FIG. 5, a portion of the medical device 10 is illustrated, including the outer needle 12 having an outer lumen 14 formed centrally therethrough with a tip 19 and a first opening 16 at its distal end 18. In this embodiment, a different variation of an inner cannula 120 is provided. The inner cannula 120 of FIG. 5 is preferably biasedly closed at its distal end 126. The distal end sides 172 are pinched shut until enough force from a fluid disposed with the inner lumen 122 pushes them apart.

Therefore, in this embodiment, the inner cannula 120 is used to inject fluid, while the outer needle 12 is used to aspirate fluid. The biasedly closed configuration of the distal end 126 of the inner cannula 120 prevents cross-contamination between the injection fluid within the inner lumen 122 and the fluid being aspirated through the outer lumen 14. Thus, the fluid being aspirated does not flow into the injection lumen 122 because it is pinched shut.

The inner cannula 120 may be formed of any suitable material, such as biocompatible stainless steel (for example, stainless steel 304), Inconel, or Nitinol, by way of example. In some embodiments, the inner cannula 120 is preferably formed of a polymer, such as polyethylene, polypropylene, PEEK, polycarbonate, polyamide, polyester, or any other plastic, by way of example.

Figure 6:
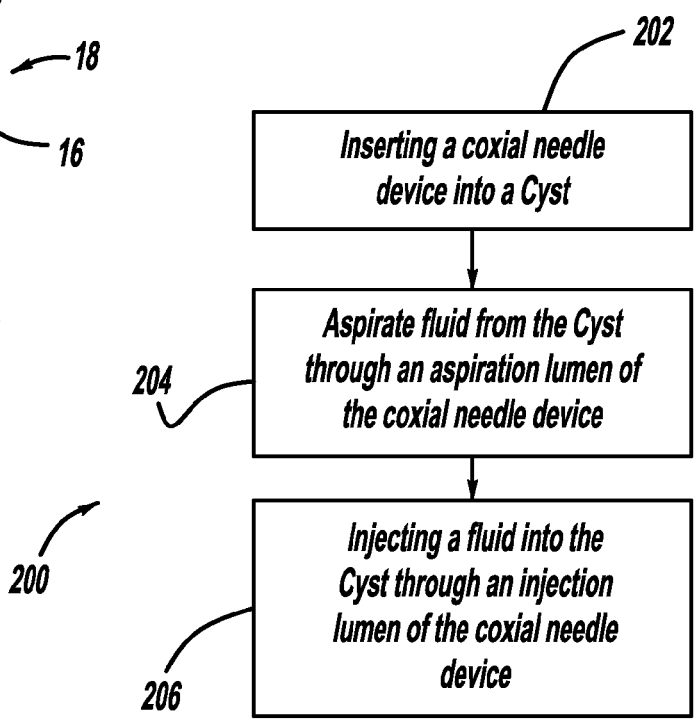
FIG. 6 is a block diagram of a method for the treatment of a cyst, in accordance with one example of the present invention.

Referring now to FIG. 6, a method 200 for the treatment of a cyst is illustrated in a block diagram. Preliminary steps of the method 200 could include, by way of example, removing a medical device 10 from packaging and inspecting same for damage and functionality. The outer lumen 14 and the inner lumen 22, 122 may be flushed with saline solution to bleed air from their passageways. A first empty syringe 32 may be attached to the medical device 10 and fluidly connected to the lumen that will be used for aspiration. A second syringe including an injection fluid, such as 0.9% saline solution, may be attached to the medical device 10 and fluidly connected to the lumen that will be used for injection.

The method 200 includes a step 202 of inserting a dual-lumen needle device, such as the medical device 10, into a cyst. For example, the dual-lumen needle device 10 may be inserted through the overlying tissues to gain access to the sac of the cyst for which treatment is desired. The dual-lumen needle device 10 includes an outer needle 12 defining an outer lumen 14 extending through the outer needle 12 and an inner cannula 20, 120 disposed within the outer lumen 14. The inner cannula 20, 120 defines an inner lumen 22, 122 extending through the inner cannula 20, 120. The dual-lumen needle device 10 may have a first syringe 32 fluidly connected to the outer lumen 14 and a second syringe 44 fluidly connected to the inner lumen 22, 122.

In addition, the method 200 includes a step 204 of aspirating fluid from the cyst through an aspiration lumen. The aspiration lumen may be either the outer lumen 14 or the inner lumen 20, 120.

The method 200 further includes a step 206 of injecting an injection fluid into the cyst through an injection lumen. The injection lumen is the other of the outer lumen 14 and the inner lumen 22, 122 that is not the aspiration lumen. For example, if the inner lumen 22, 122 is the injection lumen, then the outer lumen 14 is the aspiration lumen. Likewise, if the outer lumen 14 is used as the injection lumen, then the inner lumen 22, 122 will be the aspiration lumen. It should be understood that in some embodiments, fluid may also be injected through the aspiration lumen or aspirated through the injection lumen, for example, in additional steps of the method 200. The injection fluid may be a rinsing fluid or a treatment agent, by way of example.

After fluid is injected into the cyst through the injection lumen, the method 200 may further include a step of removing the injection fluid from the cyst through the aspiration lumen. For example, if the injection fluid was a rinsing fluid, then it may be removed. The method 200 may include repeating the steps of injecting the injection fluid, such as a rinsing fluid, into the cyst, and removing/aspirating the injection fluid from the cyst, such that these steps are performed serially.

For example, after inserting the dual-lumen needle device 10 into the cyst, fluid may be aspirated from the cyst through the aspiration lumen, such as the outer lumen 14. The volume of the cystic fluid should be carefully noted. Then, a volume of rinsing fluid, such as saline solution, approximately equal to the volume of cystic fluid may be injected into the cyst through the injection lumen, such as the inner lumen 22, 122. The rinsing fluid may then be aspirated through the aspiration lumen 14, and another volume of rinsing fluid may be injected into the cyst through the injection lumen 22, 122. The rinsing and aspirating steps may be repeated until each has been performed a total or five or more times, by way of example. In such embodiments, a syringe connected to the injection lumen, such as the second syringe 42, may be provided large enough to hold a rinsing fluid volume that is five or six times that of the cyst fluid volume. Accordingly, the second syringe 42 could remain intact and without the need for refilling between aspiration and injection steps because the second syringe 42 could hold enough volume of rinsing fluid to be able to inject a cyst-full volume into the cyst five or six (or any desired number of) times.

After one or more injection steps, one or more stopcocks 56, 58 that are fluidly connected to the syringes 32, 44 and lumens 14, 22 may be closed, and one of the syringes 32, 44 may be removed. A third syringe may be attached to the medical device 10 in the place of one of the first and second syringes 32, 44 that was removed.

The method 200 may include injecting a therapeutic agent or treatment agent into the cyst through the injection lumen 22, 122 or through the aspiration lumen 14. This step could be performed, for example, after the multiple rinsing and aspiration steps described above. The therapeutic agent may be injected through the third syringe that is attached to the medical device 10 in place of one of the first and second syringes.

For example, the third syringe may be attached in place of the first syringe 32, which was previously used for aspiration. If the third syringe is attached in the place of the first syringe 32, in this example, the therapeutic agent will then be injected through the aspiration lumen 14. The therapeutic agent may be Sodium Tetradecal Sulfate, by way of example.

In some variations, the second syringe 44 may then be removed, while one or more of the stopcocks 56, 58, such as the second stopcock 58, are closed. A fourth syringe may then be fluidly connected to the lumen that was first used as the injection lumen. The fourth syringe may contain ethanol, and ethanol may then be injected into the cyst. In this example, if the fourth syringe is connected in place of the second syringe 44, the ethanol will be injected through the injection lumen 22, 122.

One method of treatment may include injecting the therapeutic agent into the cyst for a therapeutic period of time. For example, a full-cyst volume of therapeutic agent may be injected. The therapeutic agent may then be aspirated through the same lumen through which it was injected. The first stopcock 56 may then be closed to block off the used therapeutic agent. The second stopcock 58 may then be opened, and the ethanol may be injected through the fourth syringe. A half-cyst volume of ethanol may be used to ablate the inner surface of the cyst.

Therefore, the present method 200 provides a way of aspirating fluid from a cyst and injecting fluid into a cyst through two distinct passageways within the same medical device: an aspiration lumen and an injection lumen. Accordingly, the fluid may be aspirated and injected serially, with each injecting and aspirating step immediately follow each other. Moreover, the steps may be performed with one hand, if desired. Further, the medical device 10 may be configured to provide little or no cross-contamination between the fluid being injected and the fluid being aspirated.

As a person skilled in the art will readily appreciate, the above description is meant as an illustration of the implementation of the principles of the invention. This description is not intended to limit the scope for application of this invention in that the invention is susceptible to modification, variation, and change, without departing from the spirit of this invention as defined in the following claims.

The invention claimed is:

1. A medical device for aspirating fluid from and injecting fluid into a body cavity for use with first and second syringes, the device comprising:
   an outer needle having an outer lumen formed through the outer needle and a first opening at a distal end, the first opening being in fluid communication with the outer lumen, the distal end of the outer needle configured to puncture tissue for insertion of the outer needle into the body cavity;
   an inner cannula disposed within the outer lumen, the inner cannula having an inner lumen formed through the inner cannula and a second opening at a distal end of the inner cannula, the second opening being biasingly closed and in fluid communication with the inner lumen, the distal end of the inner cannula being disposed within the outer needle lumen; and
   a hub having a first hub opening for fluidly connecting the first syringe to the outer needle lumen and a second hub opening for fluidly connecting the second syringe to the inner cannula lumen, the inner cannula being disposed within the outer needle lumen from at least one of the first and second hub openings to the distal end of the inner cannula.

2. The medical device of claim 1, wherein the inner cannula is coaxially disposed within the outer lumen.

3. The medical device of claim 2, wherein the outer lumen defines a longitudinal axis extending centrally therethrough, one of the first and second hub openings being coaxially aligned with the outer lumen and the inner lumen along the longitudinal axis to provide coaxial alignment between the lumens and a syringe.

4. The medical device of claim 3, further comprising a first syringe fluidly connected to the first hub opening and a second syringe fluidly connected to the second hub opening.

5. The medical device of claim 4, wherein the second hub opening is coaxially aligned with the outer lumen and the inner lumen along the longitudinal axis, and wherein the second syringe is coaxially aligned with the outer lumen, the inner lumen, and the second hub opening along the longitudinal axis.

6. The medical device of claim 5, the first syringe being offset a distance D from the longitudinal axis.

7. The medical device of claim 6, wherein the distance D is large enough such that the first and second syringes remain free from contact with each when the medical device is operated.

8. The medical device of claim 6, the first syringe defining an offset axis extending centrally therethrough, the offset axis being parallel to the longitudinal axis such that the first and second syringes are arranged parallel to each other.

9. The medical device of claim 1, further comprising a valve fluidly connected to one of the first and second hub openings, the valve operable to restrict fluid from flowing through the hub opening.

10. The medical device of claim 9, wherein the valve is a first valve fluidly connected to the first hub opening, the medical device further comprising a second valve fluidly connected to the second hub opening, the second valve being operable to restrict fluid from flowing through the second hub opening.

11. The medical device of claim 10, wherein each valve is one of a:
   stopcock valve and a one-way valve.

12. The medical device of claim 1, wherein the inner cannula is fixedly attached to the hub.

13. The medical device of claim 12, wherein the outer needle is fixedly attached to the hub.

14. The medical device of claim 1, wherein the first hub opening is longitudinally displaced along the longitudinal axis from the second hub opening.

15. A medical device for aspirating and injecting fluid into a body cavity, the device comprising:
   an outer needle having an outer lumen formed through the outer needle and a first opening at a distal end, the first opening being in fluid communication with the outer lumen, the distal end of the outer needle configured to puncture tissue for insertion of the outer needle into the body cavity;
   an inner cannula disposed within the outer lumen, the inner cannula having an inner lumen formed through the inner cannula, the second opening being in fluid communication with the inner lumen, and the inner cannula defining a biasingly closed opening at a distal end of the inner cannula, the distal end of the inner cannula being disposed within the outer lumen;
   a hub attached to the outer needle and the inner cannula;
   a first syringe fluidly connected to the outer lumen through a first hub opening; and
   a second syringe fluidly connected to the inner lumen through a second hub opening, wherein the inner cannula is coaxially disposed within the outer lumen from at least one of the first and second hub openings to the distal end of the inner cannula.

16. The medical device of claim 15, wherein the outer lumen defines a longitudinal axis extending centrally therethrough, one of the first and second syringes being coaxially aligned with the outer lumen and the inner lumen along the longitudinal axis.

17. The medical device of claim 16, the first and second syringes having syringe lumens, wherein one of the first and second syringes is offset a distance D from the longitudinal axis and defines an offset axis extending centrally through its syringe lumen.

18. The medical device of claim 17, wherein the distance D is large enough such that the first and second syringes remain free from contact with each other when the medical device is operated.

19. The medical device of claim 17, wherein the offset axis is parallel to the longitudinal axis and the first and second syringes are arranged parallel to each other.

20. The medical device of claim 17, wherein the first hub opening is longitudinally displaced along the longitudinal axis from the second hub opening.

21. The medical device of claim 15, further comprising a first valve operable to restrict fluid from flowing through the outer needle and a second valve operable to restrict fluid from flowing through the inner cannula.

\* \* \* \* \*